United States Patent [19]

Eicken et al.

[11] Patent Number: 5,362,876
[45] Date of Patent: Nov. 8, 1994

[54] SALICYLALDEHYDE AND SALICYLIC ACID DERIVATIVES AND SULFUR ANALOGS THEREOF, THEIR PREPARATION AND INTERMEDIATES THEREFOR

[75] Inventors: Karl Eicken, Wachenheim; Joachim Rheinheimer; Uwe J. Vogelbacher, both of Ludwigshafen; Karl-Otto Westphalen, Speyer; Matthias Gerber, Mutterstadt; Helmut Walter, Obrigheim, all of Germany

[73] Assignee: BASF Aktiengesellschaft, Ludwigshafen, Germany

[21] Appl. No.: 145,132

[22] Filed: Nov. 3, 1993

Related U.S. Application Data

[62] Division of Ser. No. 805,211, Dec. 11, 1991, Pat. No. 5,308,828.

[30] Foreign Application Priority Data

Dec. 14, 1990 [DE] Germany .................. 4039940
Aug. 10, 1991 [DE] Germany .................. 4126935

[51] Int. Cl.$^5$ .................................... C07D 491/048
[52] U.S. Cl. ................................................ 544/278
[58] Field of Search ..................................... 544/278

[56] References Cited

U.S. PATENT DOCUMENTS 5,103,006  4/1992  Rounyak .................. 544/278

Primary Examiner—Mark L. Berch
Attorney, Agent, or Firm—Keil & Weinkauf

[57] ABSTRACT

Sulfones of the formula III

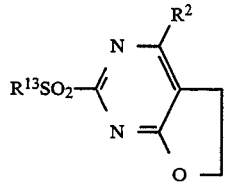

where
$R^2$ and $R^{13}$ are as defined in the specification. The sulfones are used as intermediates in preparing salicylaldehydes and salicylic acid derivatives and sulfur analogs thereof.

2 Claims, No Drawings

SALICYLALDEHYDE AND SALICYLIC ACID DERIVATIVES AND SULFUR ANALOGS THEREOF, THEIR PREPARATION AND INTERMEDIATES THEREFOR

This is a divisional of application Ser. No. 07/805,211, filed Dec. 11, 1991, U.S. Pat. No. 5,308,825.

The present invention relates to salicylaldehyde and salicylic acid derivatives and sulfur analogs thereof of the formula I

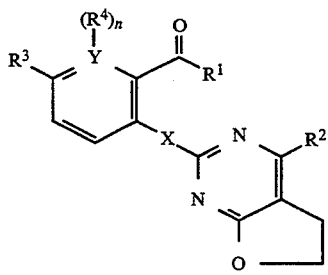

where $R^1$ is hydrogen;

a succinylimidooxy group;

a 5-membered heteroaromatic structure which contains from one to three nitrogen atoms and may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

a radical —$OR^5$, where $R^5$ is hydrogen, an alkali metal cation, one equivalent of an alkaline earth metal cation or an organic ammonium ion;

$C_3$–$C_{12}$-cycloalkyl which may carry from one to three $C_1$–$C_4$-alkyl radicals;

$C_1$–$C_{10}$-alkyl which may carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxycarbonyl, $C_3$–$C_{12}$-cycloalkyl, phenyl, phenoxy or phenylcarbonyl, where the aromatic radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_1$–$C_{10}$-alkyl which may carry from one to five halogen atoms and carries one of the following radicals: a 5-membered heteroaromatic structure which contains from one to three nitrogen atoms or one nitrogen atom and one oxygen or sulfur atom and may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio:

$C_2$–$C_6$-alkyl which carries one of the following radicals in the 2-position: $C_1$–$C_6$-alkoximino, $C_3$–$C_6$-alkenyloximino, $C_3$–$C_6$-haloalkenyloximino or benzyloximino;

$C_3$–$C_6$-alkenyl or $C_3$–$C_6$-alkynyl, where these groups in turn may carry from one to five halogen atoms;

phenyl which is unsubstituted or monosubstituted to trisubstituted by $C_1$–$C_4$-alkyl or $C_1$–$C_4$-alkoxy or monosubstituted to pentasubstituted by halogen;

an unsubstituted or substituted 5-membered aromatic heterocylic structure which has from one to four nitrogen atoms in the ring and is bonded via a nitrogen atom;

a group —$N{=}CR^6R^7$, where $R^6$ and $R^7$ are each $C_1$–$C_{20}$-alkyl which may carry phenyl, $C_1$–$C_4$-alkoxy and/or $C_1$–$C_4$-alkylthio, or are each phenyl or together form a $C_3$–$C_{12}$-alkylene chain which may carry from one to three $C_1$–$C_3$-alkyl groups;

a radical

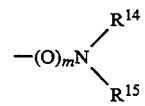

where m is 0 or 1 and $R^{14}$ and $R^{15}$ may be identical or different and have the following meanings:

hydrogen;

$C_1$–$C_6$-alkyl, $C_3$–$C_6$-alkenyl, $C_3$–$C_6$-alkynyl, where these radicals may each carry from one to five halogen atoms and/or one or two of the following groups: $C_1$–$C_6$-alkoxy, $C_3$–$C_6$-alkenyloxy, $C_3$–$C_6$-alkynyloxy, $C_1$–$C_6$-alkylthio, $C_3$–$C_6$-alkenylthio, $C_3$–$C_6$-alkynylthio, $C_1$–$C_6$-haloalkoxy, cyano, $C_1$–$C_6$-alkylcarbonyl, $C_3$–$C_6$-alkenylcarbonyl, $C_3$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, bis-$C_1$–$C_6$-dialkylamino, $C_3$–$C_6$-cycloalkyl or unsubstituted or substituted phenyl;

unsubstituted or substituted $C_3$–$C_6$-cycloalkyl;

unsubstituted or substituted phenyl;

$R^6$ together with $R^7$ form a 4-membered to 7-membered alkylene chain which is unsubstituted or substituted and in which one $CH_2$ group may be replaced with oxygen, sulfur or —NH;

a group

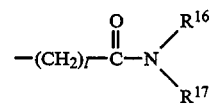

where $R^{16}$ and $R^{17}$ may be identical or different and are each hydrogen, $C_1$–$C_6$-alkyl, $C_3$–$C_6$-alkenyl or $C_3$–$C_6$-alkynyl and l is 1, 2, 3 or 4;

or a group

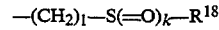

where $R^{18}$ is $C_1$–$C_6$-alkyl, $C_3$–$C_6$-alkenyl or $C_3$–$C_6$-alkynyl, l is 1, 2, 3 or 4 and k is 0, 1 or 2;

a radical $OR^5$, where $R^5$ is a group

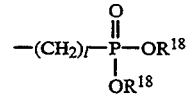

where $R^{18}$ and l have the abovementioned meanings;

or a radical

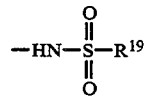

where $R^{19}$ is $C_1$-$C_6$-alkyl or phenyl, which in turn may carry from one to four of the following substituents: halogen, nitro, cyano or $C_1$-$C_6$-alkyl;

$R^2$ is $C_1$-$C_4$-alkyl, $C_1$-$C_4$-alkoxy, $C_1$-$C_4$-haloalkoxy or halogen;

$R^3$ is hydrogen or, together with $R^4$, is a group $CH_2$=CH—CH=$CH_2$ or N=CH—CH=$CH_2$;

$R^4$ is hydrogen, halogen, $C_1$-$C_4$-alkoxy, $C_1$-$C_4$-haloalkoxy, aryloxy, $C_1$-$C_4$-haloalkyl, formyl or $C_1$-$C_8$-alkoxycarbonyl; an unsubstituted or monosubstituted to trisubstituted or, where halogen is a substituent, monosubstituted to pentasubstituted phenyl radical

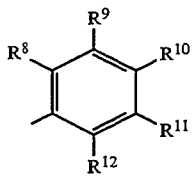

where $R^8$, $R^9$, $R^{10}$, $R^{11}$ and $R^{12}$ are each hydrogen, halogen, cyano or nitro;

$C_3$-$C_6$-alkenyl, $C_3$-$C_6$-alkenyloxy, $C_3$-$C_6$-alkynyloxy or $C_3$-$C_6$-alkynyl, where these groups in turn may carry from one to five halogen atoms;

di-$C_1$-$C_4$-alkylamino, $C_3$-$C_8$-cycloalkyl which may carry from one to three $C_1$-$C_4$-alkyl radicals;

$C_1$-$C_{10}$-alkoxycarbonyl, $C_1$-$C_4$-alkylthio;

phenoxy where the aromatic radical may carry from one to five halogen atoms and/or from one to three of the following radicals: $C_1$-$C_4$-alkyl, $C_1$-$C_4$-haloalkyl, $C_1$-$C_4$-haloalkoxy, $C_1$-$C_4$-alkoxy or $C_1$-$C_4$-alkylthio;

$C_1$-$C_{10}$-alkyl or -alkoxy which may carry from one to five halogen-atoms and/or one of the following radicals: $C_1$-$C_4$-alkoxy, $C_1$-$C_4$-alkylthio, phenyl or phenoxy, where the aromatic radicals in turn may carry from one to five halogen atoms and/or from one to three of the following radicals: $C_1$-$C_4$-alkyl, $C_1$-$C_4$-haloalkyl, $C_1$-$C_4$-haloalkoxy or $C_1$-$C_4$-alkylthio;

or $R^4$ is a 5-membered heteroaromatic structure having from one to four nitrogen atoms or one or two nitrogen atoms and in addition one sulfur or oxygen atom in the ring, or is a benzofused 5-membered heteroaromatic structure having from one to three nitrogen atoms or one nitrogen atom and in addition one oxygen or sulfur atom in the ring,- which heteroaromatic structures may carry from one to three halogen atoms and/or from one to three of the following radicals: nitro, cyano, $C_1$-$C_4$-alkyl, $C_1$-$C_4$-alkylthio, $C_1$-$C_4$-haloalkyl or phenyl which is unsubstituted or substituted by from one to three halogen atoms and/or from one to three methyl groups;

a thienyl or benzothienyl radical which may carry from one to three halogen atoms and/or from one to three of the following radicals: $C_1$-$C_4$-alkyl, $C_1$- or $C_2$-haloalkyl or nitro;

an unsubstituted or substituted naphthyl or quinolyl radical;

or oxygen when Y is nitrogen and n is 1;

n is 1 when Y is carbon or when Y is nitrogen and $R^4$ is oxygen, and 0 when Y is nitrogen and $R^4$ is not oxygen; X is oxygen or sulfur, and Y is nitrogen when $R^3$ is hydrogen and n is 0 or when $R^4$ is oxygen and n is 1; carbon when $R^3$ and $R^4$ together form a group $CH_2$=CH—CH=$CH_2$ or N=CH—CH=$CH_2$ and carbon when $R^3$ is hydrogen and n is 1;

and environmentally compatible salts of the compounds I.

In the abovementioned definitions, the expression unsubstituted or substituted means in each case that the groups thus defined may carry one or more, in particular from one to three, of the following substituents: halogen, nitro, cyano, $C_1$-$C_6$-alkyl, $C_1$-$C_6$-haloalkyl, $C_1$-$C_6$-alkoxy or $C_1$-$C_6$-alkylthio.

The present invention furthermore relates to processes for the preparation of the compounds I and their use as herbicides and growth regulators, and to novel sulfones of the formula III

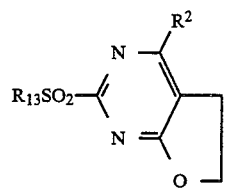

as intermediates for the preparation of the compounds of the formula I. In the formula III, $R^2$ is $C_1$-$C_4$-alkyl, $C_1$-$C_4$-alkoxy, $C_1$-$C_4$-haloalkoxy or halogen and $R^{13}$ is $C_1$-$C_{12}$-alkyl or is phenyl which is unsubstituted or substituted by alkyl, halogen or alkoxy.

The literature (EP-A 223 406, EP-A 249 708, EP-A 287 072, EP-A 287 079 and EP-A 426 476) describes herbicidal substituted salicylic acids and sulfur analogs thereof. However, their action is unsatisfactory.

It is an object of the present invention to provide novel salicylic acid derivatives and sulfur analogs thereof having improved herbicidal properties and possessing plant growth-regulating properties or other properties useful in crop protection.

We have found that this object is achieved by the compounds of the formula I which are defined at the outset. We have also found processes for the preparation of the compounds I and methods for controlling undesirable plant growth with the compounds I. We have furthermore found that salicylic acid derivatives of the general formula I defined above have excellent plant growth-regulating properties as well as good fungicidal and nitrification-inhibiting properties. We have also found novel intermediates for the preparation of the compounds I—the sulfones III.

Compounds of the formula I are obtained, for example, by reacting a correspondingly substituted salicylic acid derivative of the formula II with a corresponding compound of the formula III in the presence of a base.

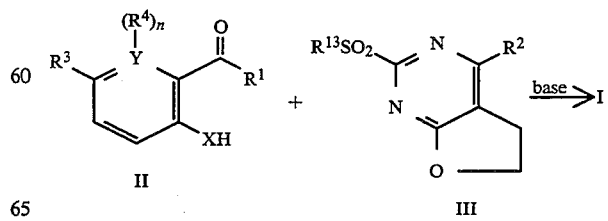

In formula III, $R^{13}SO_2$ is a conventional nucleofugic leaving group, for example arylsulfonyl, such as phenylsulfonyl or substituted phenylsulfonyl, suitable substituents being one or more, for example from 1 to 3, low molecular weight alkyl or alkoxy radicals, such as $C_1$-$C_4$-alkyl or -alkoxy, or halogen, e.g. chlorine, fluorine or bromine; or alkylsulfonyl, such as $C_1$-$C_4$-alkylsulfonyl, e.g. methylsulfonyl. Suitable bases are alkali metal or alkaline earth metal hydrides, such as NaH and $CaH_2$, alkali metal hydroxides, such as NaOH and KOH, alkali metal alcoholates, such as potassium tert-butylate, alkali metal carbonates, such as $Na_2CO_3$ and $K_2CO_3$, alkali metal amides, such as $NaNH_2$ and lithium diisopropylamide, or tertiary amines. When an inorganic base is used, it is possible to add a phase transfer catalyst if this increases the conversion.

The sulfones of the general formula III are obtained by oxidizing a corresponding 2-alkylthio- or 2-phenylthio-5,6-dihydrofuran[2,3-d]pyrimidine (cf. Collect. Czech. Chem. Commun. 32 (1967), 1582)

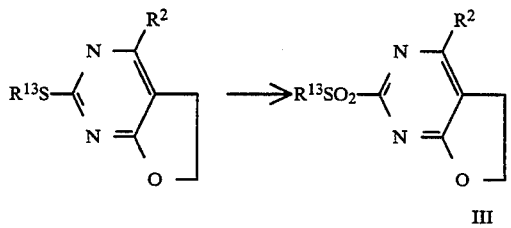

with an oxidizing agent, e.g. chlorine in water or hydrogen peroxide in glacial acetic acid, under mild conditions.

The intermediates of the formula II are in some cases known or can be .prepared by conventional methods starting from known intermediates (cf. for example EP-A-249 707, EP-A-315 889 or Japanese Preliminary Published Application 2 056 469, Application No. 310741 of Dec. 8, 1987). The following intermediates of the formula II form the subject of the prior German Application P 39 19 435.3 of Jun. 14, 1989 and, when X is oxygen and A is an aromatic or heteroaromatic structure bonded via a carbon atom, can be synthesized according to the scheme below from a 1,3-dicarbonyl compound IV (where $R^5$ is unsubstituted or phenyl-substituted $C_1$-$C_{10}$-alkyl, in particular $C_1$-$C_4$-alkyl) and an α,β-unsaturated ketone V:

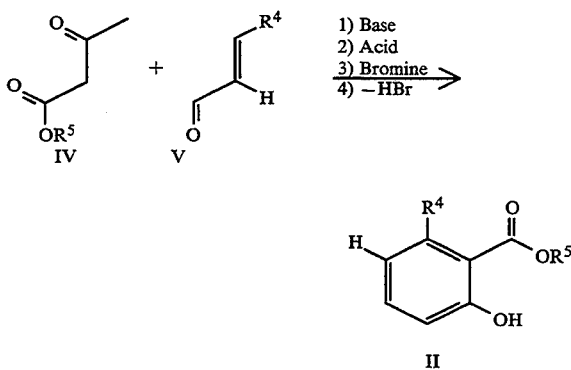

($R^4$ = aromatic or heteroaromatic structure bonded via carbon atom)

Alternatively, the intermediates of the formula II can also be prepared according to the scheme below from a methylenephosphorane IV' (Ph=phenyl) and an α,β-unsaturated ketone V:

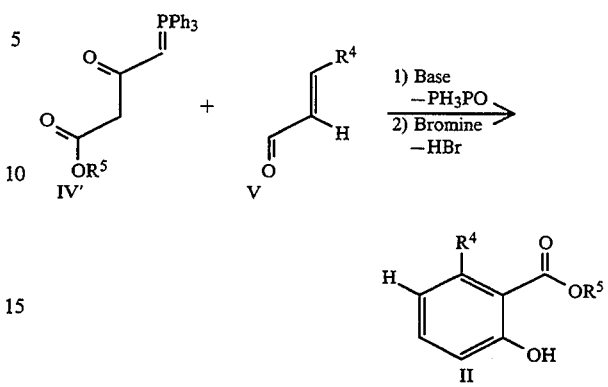

($R^4$ = aromatic or heteroaromatic structure bonded via carbon atom)

The compounds IV, IV' and V are generally known or can readily be prepared by the conventional processes. Suitable bases are the abovementioned compounds. Suitable acids are strong acids, for example hydrochloric acid, hydrobromic acid, tetrafluoboric acid, toluenesulfonic acid and trifluoroacetic acid. The elimination of hydrogen bromide can be carried out thermally or in the presence of a base, for example an organic amine.

If $R^4$ in formula II is a heteroaromatic structure bonded via a nitrogen atom and X is an oxygen atom, this intermediate can be synthesized according to the following scheme:

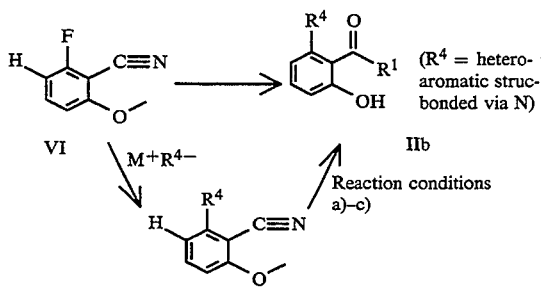

| a) 1. HCl/ethanol | b) 1. OH⁻/water | c) 1. H⁺/water |
| 2. HCl/water | 2. H⁺/water | 2. HBr, HI |
| 3. $BBr_3$ | 3. HBr, HI or $BBr_3$ | or $BBr_3$ |

$M^+R^{4-}$ is the particular alkali metal azolide. Suitable alcohols for the cleavage of the nitrile VII according to variant a) are, in particular, $C_1$-$C_4$-alkyl alcohols.

The intermediates of the formula II which are prepared as described above are usually obtained as alkyl esters. They can be hydrolyzed by known methods to give the carboxylic acids. The latter can then be converted by methods known from the literature into various esters which are required for the preparation of active ingredients of the formula I as claimed in claim 1.

Alternatively, the intermediates of the formula VII can be reacted by generally known methods with alkali metal hydroxides or tetraalkylammoniumhydroxides to give the corresponding amides and then with mineral acids, for example concentrated hydrochloric acid, to give the carboxylic acids and subsequently with concentrated hydrobromic acid to give the salicylic acids IIb. These steps can, if required, be carried out without isolation of the intermediates.

If the compounds of the formula I which are prepared in the manner described are carboxylic acids (i.e. if $R^1$ is hydroxyl), other compounds described can also be prepared therefrom, for example by first converting the carboxylic acid in a conventional manner into an activated form, such as a halide or an imidazolide, and then reacting this with the corresponding hydroxy compound. These last two steps can also be simplified, for example, by allowing the carboxylic acid to act on the hydroxy compound in the presence of a water-eliminating agent, such as a carbodiimide.

With regard to their activity, preferred compounds I are those in which the substituents have the following meanings:

$R^1$ is hydrogen, succinylimidooxy, 5-membered hetaryl, such as pyrrolyl, pyrazolyl, imidazolyl or triazolyl, in particular imidazolyl or pyrazolyl, where the aromatic radical is bonded via nitrogen and in turn may carry from one to four halogen atoms as stated above, in particular fluorine or chlorine, and/or one or two of the following radicals: alkyl, such as methyl, ethyl, propyl, 1-methylethyl, butyl, 1-methylpropyl, 2-methylpropyl or 1,1-dimethylethyl, preferably methyl, ethyl or 1-methylethyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl;

alkoxy as stated above, having from one to four carbon atoms, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy and/or alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

a radical $OR^5$, where $R^5$ is hydrogen, the cation of an alkali metal or the cation of an alkaline earth metal, such as lithium, sodium, potassium, calcium, magnesium or barium, or an environmentally compatible organic ammonium ion;

alkyl, in particular methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl or octyl, which may carry from one to five of the abovementioned halogen atoms, in particular fluorine or chlorine, and/or one of the following radicals: cyano, alkoxy or alkylthio having from one to four carbon atoms as stated above, in particular methoxy, ethoxy, 1-methylethoxy or methylthio;

alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, n-hexyloxycarbonyl, 1-methylpentyloxycarbonyl, 2-methylpentyloxycarbonyl, 3-methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentyloxycarbonyl, 2-ethylpentyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl;

phenyl, phenoxy or phenylcarbonyl, where these aromatic radicals in turn may carry from one to five halogen atoms as stated above, in particular fluorine, chlorine or bromine and/or from one to three of the following radicals: alkyl, haloalkyl, alkoxy, haloalkoxy and/or alkylthio, each having from one to four carbon atoms, as stated above in general and in particular, or 5-membered hetaryl which has from one to four nitrogen atoms in the ring, is bonded via a nitrogen atom and may carry from one to four of the radicals mentioned as being unsubstituted or substituted. Particular examples are 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 4-iodo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl or 1-benzotriazolyl;

$C_1$–$C_{10}$-alkyl as stated above which may carry from one to five halogen atoms, such as fluorine, chlorine, bromine or iodine, in particular fluorine or chlorine, and additionally carries one of the following radicals: 5-membered hetaryl having from one to three nitrogen atoms as stated above for $R^1$, where the aromatic ring may be bonded via nitrogen or carbon, or 5-membered hetaryl containing a nitrogen atom and an oxygen or sulfur atom, which carries alkyl, haloalkyl, alkoxy or alkylthio as stated under $R^1$ as substituents;

$C_2$–$C_6$-alkyl, in particular $C_2$–$C_4$-alkyl, which is substituted in the 2-position by $C_1$–$C_6$-alkoximino, e.g. methoximino, ethoximino or propoximino; $C_3$–$C_6$-alkenyloximino, such as 2-propenyloximino, 2-butenyloximino or 3-butenyloximino; $C_3$–$C_6$-haloalkenyloximino, such as 3,3-dichloro-2-propenyloximino or 2,3,3-trichloro-2-propenyloximino or benzyloximino;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl;

alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propynyl, where these alkenyl and alkynyl groups may carry from one to five of the halogen atoms stated above in general and in particular; or $R^5$ is $C_3$–$C_{12}$-cycloalkyl, in particular $C_3$–$C_6$-cycloalkyl, such as cyclopropyl, cyclobutyl, cyclopentyl or cyclohexyl, which is unsubstituted or substituted by from one to three $C_1$–$C_4$-alkyl radicals;

phenyl which is unsubstituted or monosubstituted to trisubstituted by $C_1$–$C_4$-alkyl or $C_1$–$C_4$-alkoxy, such as methyl, ethyl, propyl, butyl, methoxy or ethoxy, or phenyl which is substituted by from one to five halogen atoms, e.g. chlorine or fluorine;

a radical —N═$CR^6R^7$, where $R^6$ and $R^7$ are each straight-chain or branched $C_1$–$C_{20}$-alkyl, preferably $C_1$–$C_{15}$-alkyl, in particular $C_1$–$C_9$-alkyl, which may carry phenyl, $C_1$–$C_4$-alkoxy or $C_1$–$C_4$-alkylthio; or are each phenyl or together form $C_3$–$C_{12}$-alkylene, preferably $C_4$–$C_7$-alkylene, which may carry from one to three $C_1$–$C_3$-alkyl groups, preferably methyl or ethyl groups;

or $R^1$ is a radical

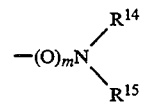

where m is 0 or 1 and $R^{14}$ and $R^{15}$ are each in general and in particular the alkyl, alkenyl, alkynyl, cycloalkyl or phenyl groups which are stated for $R^5$ and may be substituted by halogen, such as fluorine, chlorine or bromine, or by alkoxy or by alkylthio as stated for $R^1$ or by alkylcarbonyl or alkoxycarbonyl as stated for $R^5$; examples of the group —$NR^{14}R^{15}$ are the following radicals: dimethylamino, tert-butylamino, cyclohexylamino, 1-cyano-1-cyclohexylamino, isopropylamino, sec-butylamino, methylamino, diethylamino, pyrrolidinyl, 1-piperidyl, 4-morpholinyl, phenylamino and methylphenylamino;

$R^6$ together with $R^7$ is a four-membered to seven-membered, in particular four-membered to six-membered, alkylene chain which is unsubstituted or substituted by one or more of the radicals mentioned as being unsubstituted or substituted and in which a $CH_2$ group may be replaced with oxygen, sulfur or NH;

or is a group

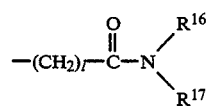

where l may be from 1 to 4, preferably 1 or 2, and $R^{16}$ and $R^{17}$ in general and in particular are each hydrogen or one of the alkyl, alkenyl or alkynyl groups stated under $R^5$, preferably methyl or ethyl;

or is a group

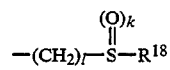

where l may be from 1 to 4, preferably 1 or 2, and $R^{18}$ in general and in particular is one of the alkyl, alkenyl or alkynyl groups stated under $R^5$, preferably methyl or ethyl;

or is a radical $OR^5$ where $R^5$ is

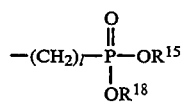

where l and $R^{18}$ have the abovementioned meanings; or is a radical

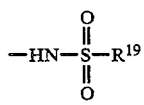

where $R^{19}$ is alkyl or unsubstituted or substituted phenyl, particularly preferably methyl, phenyl or 4-methylphenyl; $R^2$ in general and in particular is one of the alkyl, haloalkyl, alkoxy and/or haloalkoxy groups stated for $R^1$, each of from one to four carbon atoms, or halogen, such as fluorine, chlorine, bromine or iodine, in particular methyl, chlorine or methoxy;

$R^3$ is hydrogen or, together with $R^4$, is a group $CH_2=CH-CH=CH_2$ or $N=CH-CH=CH_2$, and $R^4$ is hydrogen; halogen as stated for $R^1$, in particular fluorine, chlorine or bromine;

$C_1$-$C_4$-alkoxy, such as methoxy, ethoxy, n-propoxy, isopropoxy, n-butoxy, isobutoxy or tert-butoxy;

$C_1$-$C_3$-haloalkoxy, for example $C_1$-$C_3$-alkoxy substituted by from 1 to 5 halogen atoms, such as fluorine, chlorine or bromine, e.g. trifluoromethoxy or difluoromethoxy;

aryloxy, such as phenoxy, which is unsubstituted or substituted by methyl, fluorine, chlorine or methoxy;

$C_1$-$C_4$-haloalkyl as stated for $R^1$, in particular $C_1$- or $C_2$-haloalkyl, such as trifluoromethyl;

formyl;

$C_2$-$C_8$-alkoxycarbonyl as stated specifically above for $R^1$, in particular methoxycarbonyl or ethoxycarbonyl;

unsubstituted or substituted phenyl in which suitable substituents $R^8$, $R^9$, $R^{10}$, $R^{11}$ and $R^{12}$ are halogen, such as fluorine, chlorine, bromine or iodine; cyano; nitro; unsubstituted or halogen-substituted alkenyl, alkenyloxy, alkynyloxy or alkynyl, each of from 3 to 6 carbon atoms; di-$C_1$-$C_4$-alkylamino, such as dimethylamino, diethylamino, dipropylamino, di-1-methylethylamino, dibutylamino, di-1-methylpropylamino, di-2-methylpropylamino, di-1,1-dimethylethylamino, ethylmethylamino, propylmethylamino, 1-methylethylmethylamino or butylmethylamino; unsubstituted or alkyl-substituted cycloalkyl, as stated for $R^5$, alkoxycarbonyl or alkylthio as stated for $R^5$, unsubstituted or substituted phenoxy as stated for $R^5$, $C_1$-$C_{10}$-alkyl or -alkoxy, in particular $C_1$-$C_6$-alkyl or -alkoxy, preferably $C_1$-$C_4$-alkyl or -alkoxy, which are unsubstituted or substituted by the stated radicals; the following substituted phenyl radicals are examples of $R^4$: 2-fluorophenyl, 3-fluorophenyl, 4-fluorophenyl, 2,6-difluorophenyl, 2,4-difluorophenyl, 2-fluoro-4-trifluoromethylphenyl, 2,3-difluorophenyl, 2-chlorophenyl, 3-chlorophenyl, 2-iodophenyl, 2-bromophenyl, 2-chloro-6-fluorophenyl, pentafluorophenyl, pentachlorophenyl, 2,4-dichlorophenyl, 2,6-dichlorophenyl, 2-chloro-4-fluorophenyl, 3,5-dichlorophenyl, 2-chloro-6-methylphenyl, 2,3,5-trichlorophenyl, 2-methylphenyl, 3-methylphenyl, 4-methylphenyl, 2,6-dimethylphenyl, 2,4-dimethylphenyl, 3,5-dimethylphenyl, 2,4,6-trimethylphenyl, 2-chloro-4-methylphenyl, 2-methoxyphenyl, 4-methoxyphenyl, 4-chloro2-methoxyphenyl, 2-trifluoromethylphenyl, 2,3-dimethyl-4-methoxyphenyl, 4-dimethylamino-2-methylphenyl, 3-cyanophenyl, 3-nitrophenyl, 3-phenoxyphenyl, 3-(3-trifluoro-methylphenoxy)-phenyl or 3-trifluoromethylphenyl;

unsubstituted or substituted 5-membered hetaryl or benzofused hetaryl having from 1 to 4 nitrogen atoms, as stated for $R^1$, or having one or 2 nitrogen atoms and in addition one sulfur or oxygen atom, such as unsubstituted or substituted 5-membered hetaryl having from 2 to 4 nitrogen atoms, as stated for $R^1$, or having one or 2 nitrogen atoms and in addition one sulfur or oxygen atom, such as isoxazolyl, oxazolyl, thiazolyl or thiadiazolyl.

Examples of hetaryl radicals are the following: pyrrolyl-1-yl, 1-methylpyrrol-2-yl, 1-methylpyrrol-3-yl, pyrazol-1-yt, 4-methylpyrazol-1-yl, 3,5-dimethylpyrazol-1-yl, 3,4,5-trimethylpyrazol-1-yl, 4-chloropyrazol-1-yl, 4-phenylpyrazol-1-yl, 4-isopropylpyrazol-1-yl, 4-nitropyrazol-1-yl, imidazol-1-yl, 4,5-dimethylimidazolyl, 2-methyl-4,5-dichloroimidazolyl, 4(5)-nitroimidazolyl-1-yl, [1,2,4]-triazol-1-yl, 3(5)-methyl-[1,2,4]-triazol-1-yl, [1,2,3]-triazol-1-yl, 4,5-dimethyl-[1,2,3]-triazol-1-yl, [1,2,3,4]-tetrazol-1-yl, 1-methylpyrazol-4-yl, 1-phenylpyrazol-4-yl, 1,3,5-trimethylpyrazol-4-yl, 1-methylpyrazol-5-yl, 1-phenylpyrazol-5-yl, 1-methylpyrazol-3-yl, 1-phenylpyrazol-3-yl, 1-methylimidazol-2-yl, 1-methylimidazol-5-yl, 1-phenylimidazol-5-yl, 1-phenyl-[1,2,3]-triazol-4-yl, isoxazol-5-yl, isoxazol-4-yl, 3-methylisoxasol-5-yl, 3-isopropylisoxazol-5-yl, 3-phenylisoxazol-5-yl, oxazol-2-yl, 2-methyloxazol-4-yl, thiazol-4-yl, 2-benzothiazol-4-yl, 4-methylthiazol-2-yl, 4-methylthioazol-5-yl, 4-phenylthiazol-2-yl or 2-phenylthiazol-5-yl.

Unsubstituted or substituted thienyl or benzothienyl radicals are, for example, 2-thienyl, 3-thienyl, 2,3-dichloro-4-thienyl, 2-methyl-5-thienyl, 2-nitro-5-thienyl, 2-benzothienyl and 3-benzothienyl.

Unsubstituted or substituted naphthyl or quinolyl radicals are, for example, 1-naphthyl, 2-naphthyl, 2-chloro-1-naphthyl, 6-chloro-1-naphthyl, 2,6-dichloro-1-naphthyl, 2-methyl-6-chloro-1-naphthyl, 2-quinolyl, 4-quinolyl, 6-quinolyl, 8-quinolyl and 6-methyl-2-quinolyl.

If a radical is defined as unsubstituted or substituted, it may carry one or more, in particular from one to three, of the following substituents: halogen, in particular chlorine or bromine, nitro or cyano, or alkyl, haloalkyl, alkoxy or alkylthio as stated for $R^1$.

Particularly preferred compounds of the formula I are those in which $R^2$ is methoxy, X is oxygen and Y and $R^1$, $R^3$ and $R^4$ have the meanings stated at the outset.

Suitable salts of the compounds of the formula I are environmentally compatible salts, for example alkali metal salts, in particular the potassium or sodium salt, alkaline earth metal salts, in particular the calcium, magnesium or barium salt, manganese, copper, zinc or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

The herbicidal, growth-regulating, fungicidal or nitrification-inhibiting compounds I according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are generally suitable for preparing solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably from 95 to 100, % (according to the NMR spectrum).

The compounds I according to the invention may be formulated for instance as follows:

I. 90 parts by weight of compound no. 3.008 is mixed with 10 parts by weight of N-methyl-alpha-pyrrolidone. A mixture is obtained which is suitable for application in the form of very fine drops.

II. 20 parts by weight of compound no. 3.013 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3.008 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3.008 is dissolved in a mixture consisting of 25 parts by weight of cyclohexanone, 65 parts by weight of a mineral oil fraction having a boiling point between 210 and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3.008 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3.013 is intimately mixed with 97 parts by weight of particulate kaolin. A dust is obtained containing 3% by weight of the active ingredient.

VII. 30 parts by weight of compound no. 3.013 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 3.008 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal or growth-regulating agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates of herbicidal active ingredient depend on the objective to be achieved, the time of the year, the plants to be combated and their growth stage, and are from 0.001 to 1, and preferably from 0.01 to 0.5, kg/ha.

The growth-regulating salicylic acid derivatives of the formula I may exercise a variety of influences on practically all plant development stages, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The reduction in vegetative growth is also important in fruit and other trees, thus saving on pruning costs. With growth regulators, it is also possible to break up the alternate breeding rhythm of fruit trees.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited: on the other, the young rape plants are Kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The active ingredients of the formula I may raise the yield by influencing plant metabolism or by promoting or inhibiting vegetative and/or generative plant growth.

C. It is also possible with the compounds of the formula I to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a dressing), but also to the soil, i.e., via the roots, and—the method particularly preferred—to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 10, g per kg of seed are generally required. For foliage and soil treatment, amounts of from 0.001 to 10, preferably from 0.01 to 3, and particularly from 0.01 to 0.5, kg/ha are generally considered sufficient.

In view of the numerous application methods possible, the compounds according to the invention, or agents containing them, may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

The compounds I are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits, and in the seeds of these plants.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by treating the fungi, or the plants, seed or materials to be protected against fungus attack, or the soil, with a fungicidally effective amount of the active ingredients. They may be applied before or after infection of the plants or seeds by the fungi.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*.

When the active ingredients are used for treating seed, amounts of from 0.001 to 50, and preferably from 0.01 to 10, g per kg of seed are usually required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

To increase the spectrum of action and to achieve synergistic effects, the compounds I according to the invention may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the following synthesis examples were used, after appropriate modification of the starting materials, to obtain further compounds I and II. The compounds thus obtained are given in the following tables with their physical data. Compounds without these data may be synthesized analogously from the corresponding starting materials. The structures given in Table 3 describe particularly preferred active ingredients of the formula I.

Example 1

Methyl 6-Phensylsalicylate

Variant 1

58 g (0.5 moll of methyl acetoacetate is added to a solution of 0.5 g of sodium hydride in 100 ml of dried ethanol. 66 g (0.5 moll of cinnamaldehyde is dripped in quickly and the whole is stirred for about 10 hours at room temperature. The mixture is then saturated at 0° C. with anhydrous HCl gas and then stirred for about 1 day at room temperature (20° C.). The solvent is removed and the residue is distilled under reduced pressure, HCl gas initially being liberated. The fractions distilling over at 115 to 165° C./0.2 mbar are combined and chromatographed using silica gel (eluation with toluene/cyclohexane). There is obtained 33.7 g of a yellow oil as intermediate, which is dissolved in 150 ml of methylene chloride. At 0° C. a solution of 22.9 g (0.14 mol) of bromine in 150 ml of glacial acetic acid is rapidly added, and the mixture is slowly heated and refluxed for one hour. The reaction solution is poured into 200 ml of methylene chloride and 500 ml of water. The organic phase is separated and worked up in the usual manner. A yellow solid is obtained as intermediate, which is dissolved in 400 ml of methyl tert-butyl ether for working up. 55 g (0.56 mol) of triethylamine is added and the mixture is refluxed for 5 hours. 300 ml of water is added, and the organic phase is separated off and worked up in the usual manner. The residue is distilled at 100 to 114° C./0.2 mbar. Yield: 11.9 g.

Variant 2

Under a nitrogen blanket, 8.55 g (0.3 mol) of sodium hydride (85% strength) is added in portions to a solution of 57 g (0.15 mol) of methyl 4-(triphenylphosphoranylidene)-acetoacetate in 700 ml of THF. The mixture is then heated to about 35° C. At this temperature, 20 g (0.15 mol) of cinnamaldehyde is added in portions, followed by 5 to 10 drops of water; the reaction initially proceeds exothermically and has to be cooled. It is then continued at 35° C. until the ylide has been completely reacted (checked by thin-layer chromatography, about 12 to 14 hours). The reaction mixture is acidified with 10% strength hydrochloric acid, 1 liter of water is added and the mixture is extracted four times, each time with 150 ml of ether. The combined ether phases are extracted by shaking with 200 ml of water and 200 ml of saturated sodium chloride solution, dried over sodium sulfate and evaporated down. The blackish-brown residue is taken up with 400 ml of methyl tert-butyl ether and boiled for several hours. After cooling the insoluble residue (triphenylphosphine oxide) is removed by filtration and the filtrate is evaporated down. The oil which remains is purified by chromatography using silica gel (developer: toluene/ethyl acetate with an increasing portion of ethyl acetate). All the fractions prior to the triphenylphosphine oxide are combined, and brominated, aromatized and worked up according to the instructions given above. There is obtained 14.5 g of product.

The following compounds may be prepared analogously:

Methyl 6-(3,5-dichlorophenyl)-salicylate, $^1$H-NMR (CDCl$_3$: $\delta$ = 3.58 (s; 3H); 6.70 (d; 1H); 7.05 (d; 1H); 7.10 (d; 2H); 7.25-7.40 (m; 2H); 10.85 (s; 1H).

Methyl 6-(2,4-dichlorophenyl)-salicylate, $^1$H-NMR (CDCl$_3$: $\delta$ = 3.58 (s; 3H); 6.65 (d; 1H); 7.0-7.5 (m; 5H); 11.1 (s; 1H).

Example 2

General Directions for Preparing Salicylic Acid Derivatives of the Formula I 0.073 mol of the aromatic 2-hydroxycarboxylic acid in question is dissolved in 320 ml of dried dimethyl sulfoxide. 16.4 g (0.146 mol) of potassium tert-butylate is added, the temperature of the reaction mixture rising to about 30° C. After the mixture has been cooled to room temperature, 16.8 g (0.073 mol) of 4-methoxy-2-methylsulfonyl-5,6-dihydrofuran-[2,3-d]-pyrimidine is added and the mixture is stirred for about 1 hour at room temperature. The reaction mixture is poured into about 2 liters of cold water, acidified with hydrochloric acid and extracted with methyl tert-butyl ether. After conventional working up the crude product remaining may, if necessary, be purified by stirring with a suitable solvent, or by chromatography using silica gel.

Example 3

General Directions for Preparing Salicylic Acid Derivatives of the Formula I 5.1 g of potassium hydroxide and 0.08 mol of the hydroxycarboxylic acid in question are dissolved in 80 ml of methanol. The mixture is stirred for 10 minutes at room temperature and evaporated down under reduced pressure. For drying, toluene is repeatedly added and is then evaporated at 50° C. under reduced pressure. The light red powder thus obtained is taken up in 300 ml of dimethyl sulfoxide and 2.9 g of 80% strength sodium hydride is added in portions at room temperature, gas evolution occurring. When no more gas is liberated, a solution of 0.08 mol of 4-methoxy-2-methylsulfonyl-5,6-dihydrofuran-[2,3-d]-pyrimidine in 80 ml of dimethyl sulfoxide is dripped in and the mixture is stirred for 30 minutes. It is then poured into 2 liters of water, neutralized with acetic acid and washed with methylene chloride. The mixture is strongly acidified with hydrochloric acid and extracted several times with methyl tert-butyl ether. The organic phase is dried over sodium sulfate and the solvent is evaporated off under reduced pressure. The substance remaining may be purified by chromatography using silica gel.

Example 4

General Directions for Preparing Aromatic Carboxylic Oxime Esters or Similar Compounds of the Formula I 3.2 mmol of the aromatic 2-(4-methoxy-5,6-dihydrofuran-[2,3-d]-pyrimidin-2-yl)-oxycarboxylic acid in question and 20 ml of dimethoxyethane are introduced and 3.2 mmol of sodium hydride is added. Gas immediately evolves. The mixture is stirred for 1 hour at room temperature and cooled to 0° C., and 3.5 mmol of oxalyl chloride is added. This mixture is stirred for 1 hour at 0° C. and the excess oxalyl chloride is removed by evaporating about 30% of the solvent under reduced pressure. 4.2 mmol of the oxime in question or a comparable hydroxy compound dissolved in 10 ml of dimethoxyethane is added, followed by 3.2 mmol of pyridine at 0° C., and the mixture is heated within 1 hour to room temperature. The mixture is poured into 120 ml of cold water and extracted with methylene chloride. The organic phase is dried over sodium sulfate and evaporated down under reduced pressure. The substance which remains can be further purified by chromatography using silica gel.

Example 5 a) 2-Methoxy-6-(pyrazol-1-yl)-benzonitrile:

At 50° C. and under a nitrogen blanket, a solution of 0.273 mol of sodium pyrazolide (prepared from equimolar amounts of pyrazole and sodium hydride) in 140 ml of N,N-dimethylethyleneurea is dripped into a solution of 41,2 g (0.273 mol) of 2-methoxy-6-fluorobenzonitrile (preparation: J. Heterocycl. Chem., 25, 1173, 1988) in 50 ml of N,N-dimethylethyleneurea, and the mixture is stirred for 2 hours at 60° C. The batch is cooled and stirred into 4 liters of ice water, and the crystals which precipitate are suction filtered and dried; there is obtained 37.1 g of the product of m.p. 93°–94° C.

b) 0-Ethylimino 2-methoxy-6-(pyrazol-1-yl)-benzoate

At 0° C. and while stirring, 37.1 g (0.186 mol) of 2-methoxy-6-(pyrazol-1-yl)-benzonitrile is introduced with the exclusion of moisture into 68.0 g of a 30% strength solution of dry HCl gas in ethanol. After the mixture has been diluted with 20 ml of ethanol it was stirred for 48 hours at room temperature and poured into 500 ml of ice water. A pH of 7 is set up by adding 2N caustic solution and then saturated sodium bicarbonate solution. The crystals which precipitate out are suction filtered and dried. There is obtained 30.3 g of the product of m.p. 72°–73° C.

c) Ethyl 2-methoxy-6-(pyrazol-1-yl)-benzoate:

29.0 g (0.118 mol) of 0-ethylimino 2-methoxy-6-(pyrazol-1-yl)-benzoate and 300 ml of hydrochloric acid are stirred at 50° C. for 16 hours. After the reaction mixture has been cooled it is extracted three times, each time with 100 ml of methylene chloride. After the extract has been evaporated down, 16.7 g of residue is obtained which is chromatographed on silica gel with toluene/ethyl acetate (9:1). There is obtained 13.4 g of the product of m.p. 159°–163° C.

d) Ethyl 6-(pyrazol-1-yl)-salicylate:

At 20° to 25° C., 200 ml (0.2 mol) of 1-molar boron tribromide solution is dripped into a solution of 15.3 g (0.062 mol) of ethyl 2-methoxy-6-(pyrazol-1-yl)-benzoate in 140 ml of methylene chloride. The mixture is stirred for about 10 hours at room temperature and then 160 ml of ethanol is dripped in at 0° C. This mixture is stirred for 15 minutes, the solvent is substantially removed under reduced pressure and at 30° C., and the residue is stirred with 200 ml of water. The residue is extracted three times, each time with 70 ml of diethyl ether, and evaporated down, and the crude product is chromatographed on silica gel using toluene/ethyl acetate. Yield: 8.7 g of the product as an oil. $^1$H-NMR (selected signals): δ=0.98 (t); 4.10 (q); 6.38; 6.90; 7.10; 7.45 (t); 7.60; 7.70; 10.70 (s).

Hydrolysis of this compound with dilute sodium hydroxide solution gives 6-(pyrazol-1-yl)-salicylic acid (m.p.: 175°–179° C.).

TABLE 1

Salicylic acid derivatives of the formula II

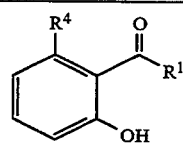

II

| No. | $R^1$ | $R^4$ | Phys. data mp. [°C.] |
|---|---|---|---|
| 1.001 | OH | 2-Fluorophenyl | |
| 1.002 | OH | 4-Fluorophenyl | 250–255 (decomp)$^{a)}$ |
| 1.003 | OH | 2,6-Difluorophenyl | |
| 1.004 | OH | 2,4-Difluorophenyl | |
| 1.005 | OH | 2-Fluoro-4-trifluoromethylphenyl | |
| 1.006 | OH | 2-Chlorophenyl | 168–179 |
| 1.007 | OH | 2-Bromophenyl | |
| 1.008 | OH | 2-Chloro-6-fluorophenyl | |
| 1.009 | OH | Pentafluorophenyl | |
| 1.010 | OH | 2,4-Dichlorophenyl | |
| 1.011 | OH | 2,6-Dichlorophenyl | |
| 1.012 | OH | 2-Chloro-4-fluorophenyl | |
| 1.013 | OH | 3,5-Dichlorophenyl | |
| 1.014 | OH | 2-Methylphenyl | 140–143 |
| 1.015 | OH | 2-Chloro-6-methylphenyl | |
| 1.016 | OH | 3-Methylphenyl | |
| 1.017 | OH | 4-Methylphenyl | |
| 1.018 | OH | 2,6-Dimethylphenyl | |
| 1.019 | OH | 3,5-Dimethylphenyl | |
| 1.020 | OH | 2,4,6-Trimethylphenyl | 75–78 |
| 1.021 | OH | 2,4-Dimethylphenyl | |
| 1.022 | OH | 2-Chloro-4-methylphenyl | |

TABLE 1-continued

Salicylic acid derivatives of the formula II

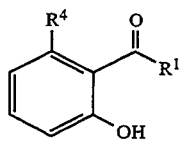

| No. | R¹ | R⁴ | Phys. data mp. [°C.] |
|---|---|---|---|
| 1.023 | OH | 2,3,5-Trichlorophenyl | |
| 1.024 | OH | 4-Methoxyphenyl | |
| 1.025 | OH | 2-Methoxyphenyl | 150–152 |
| 1.026 | OH | 4-Chloro-2-methoxyphenyl | |
| 1.027 | OH | 2-Trifluoromethylphenyl | |
| 1.028 | OH | 2,3-Dimethyl-4-methoxyphenyl | |
| 1.029 | OH | 2-Dimethylamino-2-methylphenyl | |
| 1.030 | OH | 3-Cyanophenyl | |
| 1.031 | OH | 3-Phenoxyphenyl | |
| 1.032 | OH | 3-(3-Trifluoromethylphenoxy)phenyl | |
| 1.033 | OH | 3-Trifluoromethylphenyl | |
| 1.034 | OH | 3-Bromophenyl | |
| 1.035 | OH | 3-Chlorophenyl | |
| 1.036 | OH | 4-Bromophenyl | 168–175 |
| 1.037 | OH | 4-Chlorophenyl | |
| 1.038 | OH | 4-Trifluoromethylphenyl | |
| 1.039 | OH | 3-(3,4-Dichlorophenoxy)phenyl | |
| 1.040 | OH | 4-Methylthiophenyl | |
| 1.041 | OH | 4-tert.-Butylphenyl | 210–225 (decomp)[a] |
| 1.042 | OH | Phenyl | |
| 1.043 | ONa | Phenyl | |
| 1.044 | OH | 3-Methoxyphenyl | |
| 1.045 | OH | 4-Ethoxycarbonylphenyl | |
| 1.046 | OH | Pyrazol-1-yl | 175–179 |
| 1.047 | OH | 3,5-Dimethylpyrazol-1-yl | 182 (decomp) |
| 1.048 | OH | 3(5)-Methylpyrazol-1-yl | 184 (decomp) |
| 1.049 | OH | 4-Methylpyrazol-1-yl | 162 (decomp) |
| 1.050 | OH | 4-Chloropyrazol-1-yl | 175 (decomp) |
| 1.051 | OH | 4-Bromopyrazol-1-yl | |
| 1.052 | OH | 4-Phenylpyrazol-1-yl | 200–202 |
| 1.053 | OH | 3,4,5-Trimethylpyrazol-1-yl | 180 (decomp) |
| 1.054 | OH | 4-Chlor-3,5-dimethylpyrazol-1-yl | 209–212 (decomp) |
| 1.055 | OH | 4-Isopropylpyrazol-1-yl | |
| 1.056 | OH | 3(5)-Phenylpyrazol-1-yl | 212 (decomp) |
| 1.057 | OH | 3(5)-Methyl-5(3)-phenylpyrazol-1-yl | 230–234 (decomp) |
| 1.058 | OH | 3,5-Bistrifluormethylpyrazol-1-yl | |
| 1.059 | OH | 4-Nitropyrazol-1-yl | |
| 1.060 | OH | Imidazol-1-yl | 216 (decomp) |
| 1.061 | OH | 2-Methylimidazol-1-yl | |
| 1.062 | OH | 4,5-Dimethylimidazol-1-yl | |
| 1.063 | OH | 2-Phenylimidazol-1-yl | |
| 1.064 | OH | 4,5-Dichlorimidazol-1-yl | 180 (decomp) |
| 1.065 | OH | 2,4,5-Trichlorimidazol-1-yl | |
| 1.066 | OH | 2-Methyl-4,5-dichlorimidazol-1-yl | |
| 1.067 | OH | 2-Methyl-4,5-dibromimidazol-1-yl | |
| 1.068 | OH | 4(5)-Chlor-5(4)-methylimidazol-1-yl | |
| 1.069 | OH | 4(5)-Nitroimidazol-1-yl | |
| 1.070 | OH | [1,2,4]-Triazol-1-yl | 214–215 (decomp) |
| 1.071 | OH | 3(5)-Methyl-[1,2,4]-triazol-1-yl | 210–211 (decomp) |
| 1.072 | OH | 3(5)-Phenyl-[1,2,4]-triazol-1-yl | 225 (decomp) |
| 1.073 | OH | 3,5-Dimethyl-[1,2,4]-triazol-1-yl | 255 (decomp) |
| 1.074 | OH | [1,2,4]-Triazol-1-yl | |
| 1.075 | OH | 4,5-Dimethyl-[1,2,3]-triazol-1-yl | |
| 1.076 | OH | 4(5)-Phenyl-[1,2,3]-triazol-1-yl | |
| 1.077 | OH | [1,2,4]-Tetrazol-1-yl | |
| 1.078 | OH | 1-Phenyl-pyrazol-4-yl-pyrazol-4-yl | |
| 1.079 | OH | 1,3,5-Trimethylpyrazol-4-yl | |
| 1.080 | OH | 1-Methylpyrazol-4-yl | |
| 1.081 | OH | 1-Methylpyrazol-5-yl | |
| 1.082 | OH | 1-Phenylpyrazol-5-yl | |
| 1.083 | OH | 1-Methylpyrazol-3-yl | |
| 1.084 | OH | 1-Phenylpyrazol-3-yl | |
| 1.085 | OH | 1,4-Dimethylpyrazol-3-yl | |
| 1.086 | OH | 5-Methyl-1-phenyl-pyrazol-3-yl | |
| 1.087 | OH | 1,5-Dimethylpyrazol-3-yl | |
| 1.088 | OH | 1,3-Dimethylpyrazol-4-yl | |
| 1.089 | OH | 1,5-Dimethylpyrazol-4-yl | |
| 1.090 | OH | 3-Methyl-1-phenylpyrazol-4-yl | |
| 1.091 | OH | 5-Methyl-1-phenylpyrazol-4-yl | |
| 1.092 | OH | 3,5-Dimethyl-1-phenylpyrazol-4-yl | |
| 1.093 | OH | 3-Methyl-1-phenylpyrazol-5-yl | |
| 1.094 | OH | 1,4-Dimethylpyrazol-5-yl | |

TABLE 1-continued

Salicylic acid derivatives of the formula II

II

| No. | R¹ | R⁴ | Phys. data mp. [°C.] |
|---|---|---|---|
| 1.095 | OH | 1,3-Dimethylpyrazol-5-yl | |
| 1.096 | OH | 1-Methyl-[1,2,3]-triazol-5-yl | |
| 1.097 | OH | 1-Phenyl-[1,2,4]-triazol-5-yl | |
| 1.098 | OH | 1-Phenyl-[1,2,3]-triazol-4-yl | |
| 1.099 | OH | 5-Methyl-1-phenyl-[1,2,3]-triazol-4-yl | |
| 1.100 | OH | 5-Methyl-1-phenyl-[1,2,4]-triazol-3-yl | |
| 1.101 | OH | 1-Methylimidazol-2-yl | |
| 1.102 | OH | 1,4-Dimethylimidazol-5-yl | |
| 1.103 | OH | 1-Methyl-5-nitroimidazol-2-yl | |
| 1.104 | OH | 1-Methylimidazol-5-yl | |
| 1.105 | OH | 1-Phenylimidazol-5-yl | |
| 1.106 | OH | 2-Thienyl | |
| 1.107 | OH | 3-Thienyl | |
| 1.108 | OH | 2,3-Dichloro-4-thienyl | |
| 1.109 | OH | 2,5-Dichloro-3-thienyl | |
| 1.110 | OH | 2-Bromo-5-thienyl | |
| 1.111 | OH | 4-Bromo-2-thienyl | |
| 1.112 | OH | 3-Methyl-2-thienyl | |
| 1.113 | OH | 2-Chloro-5-thienyl | |
| 1.114 | OH | 2-Methyl-5-thienyl | |
| 1.115 | OH | 2-Nitro-5-thienyl | |
| 1.116 | OH | Isoxazol-5-yl | |
| 1.117 | OH | 3-Methylisoxazol-5-yl | |
| 1.118 | OH | 3-Isopropylisoxazol-5-yl | |
| 1.119 | OH | 3-Phenylisoxazol-5-yl | |
| 1.120 | OH | 3-Methyl-4-chloroisoxazol-5-yl | |
| 1.121 | OH | 3-Methylisoxazol-4-yl | |
| 1.122 | OH | Isoxazol-4-yl | |
| 1.123 | OH | 3,5-Dimethylisoxazol-4-yl | |
| 1.124 | OH | 2-Methyloxazol-4-yl | |
| 1.125 | OH | Oxazol-2-yl | |
| 1.126 | OH | 2-Methylthiazol-4-yl | |
| 1.127 | OH | 2-Phenylthiazol-4-yl | |
| 1.128 | OH | Thiazol-4-yl | |
| 1.129 | OH | 2-Benzylthiazol-4-yl | |
| 1.130 | OH | 5-Chloro-2-phenylthiazol-4-yl | |
| 1.131 | OH | Thiazol-2-yl | |
| 1.132 | OH | Thiazol-5-yl | |
| 1.133 | OH | 4-Methylthiazol-2-yl | |
| 1.134 | OH | 5-Methylthiazol-2-yl | |
| 1.135 | OH | 4-Phenylthiazol-2-yl | |
| 1.136 | OH | 4-Methylthiazol-5-yl | |
| 1.137 | OH | 2-Methylthiazol-5-yl | |
| 1.138 | OH | 2-Phenylthiazol-5-yl | |
| 1.139 | OH | [1,3,4]-Thiadiazol-2-yl | |
| 1.140 | OH | 5-Methyl-[1,3,4]-thiadiazol-2-yl | |
| 1.141 | OH | 5-Phenyl-[1,3,4]-thiadiazol-2-yl | |
| 1.142 | OCH₃ | 1,4-Dichlorophenyl | 120–147/0.53 |
| 1.143 | OCH₃ | 3,5-Dichlorophenyl | 145–160/0.27 |
| 1.144 | OCH₃ | Pyrazol-1-yl | oil |
| 1.145 | OCH₃ | 4-Fluorophenyl | 114–135/0.27 |
| 1.146 | OCH₃ | 4-Methylphenyl | 140–147/0.8 |
| 1.147 | OCH₃ | 4-Methoxyphenyl | 156–185/0.57 |
| 1.148 | OCH₃ | 4-Nitrophenyl | 107–120 |
| 1.149 | OCH₃ | 2-Methoxyphenyl | 153–173/0.57 |
| 1.150 | OH | 4-Nitrophenyl | >300[a] |
| 1.151 | OCH₃ | 4-tert.-Butylphenyl | 158–178/0.66 |
| 1.152 | OCH₃ | 4-Phenylphenyl | 195–220/0.57 |
| 1.153 | OCH₃ | 4-Cyanophenyl | 182–215/1.33 |
| 1.154 | OH | 4-Carboxyphenyl | 210–218 (decomp) |
| 1.155 | OCH₃ | 4-Phenoxyphenyl | 203–218/0.4 |
| 1.156 | OH | 4-Phenoxyphenyl | 142–148 |
| 1.157 | OCH₃ | 4-(4′-Fluorophenoxy)-phenyl | 203–220/0.57 |
| 1.158 | OH | 4-(4′-Fluorophenoxy)-phenyl | 130–135 |
| 1.159 | OH | 4-Phenylphenyl | 175–185 |
| 1.160 | OH | 2-Nitrophenyl | 132–135 |
| 1.161 | OCH₃ | 4-Bromophenyl | 156–173/1.33 |
| 1.162 | OCH₃ | 2-Chlorophenyl | 126–151/0.4 |
| 1.163 | OCH₃ | Phenyl | 147–172/0.8 |
| 1.164 | OCH₃ | 2-Methylphenyl | 119–132/0.57 |
| 1.165 | OCH₃ | 2-Thienyl | 118–160/0.4 |
| 1.166 | OCH₃ | 3-Methylphenyl | 70–145/0.66 |

TABLE 1-continued

Salicylic acid derivatives of the formula II $$\text{II}$$

| No. | $R^1$ | $R^4$ | Phys. data mp. [°C.] |
|---|---|---|---|
| 1.167 | $OCH_3$ | 4-Chlorophenyl | 120–150/0.66 |
| 1.168 | $OCH_3$ | 2-Fluorophenyl | 80–95/0.57 |
| 1.169 | $OCH_3$ | 3-Methoxyphenyl | 160–175/0.66 |
| 1.170 | $OCH_3$ | 4-Trifluoromethylphenyl | 120–160/0.66 |
| 1.171 | OH | 4-Trifluoromethylphenyl | 120–160/0.66 |
| 1.172 | $OC_2H_5$ | Phenyl | 150–162/1.33 |
| 1.173 | OH | 3-Isopropyl-pyrazol-1-yl | 160–63 |
| 1.174 | OH | 3(5)-Methylthio-1,2,4-triazol-1-yl | 215 (decomp) |
| 1.175 | OH | 3(5)-Methylthio-5(3)-methyl-1,2,4-triazol-1-yl | 130 (decomp) |
| 1.176 | OH | 3(5)-Phenyl-5(3)-methyl-1,2,4-triazol-1-yl | 240 (decomp) |
| 1.177 | O-pyr[b] | Phenyl | |
| 1.178 | O-imi[b] | Phenyl | |
| 1.179 | O—$N(CH_3)_2$ | Phenyl | |
| 1.180 | O—NH—$C(CH_3)_3$ | Phenyl | |
| 1.181 | O-pip[b] | Phenyl | |
| 1.182 | O-mor[b] | Phenyl | |

[a]= Data of the corresponding disodium salt
[b]pyr = 1-Pyrazolyl; imi = 1-Imidazolyl; pip = 1-Piperidinyl, mor = 4-Morpholinyl Example 6

Preparation of 2-Methylsulfonyl-4-Methoxy-5,6-Dihydrofuran-[2,3-d]Pyrimidine

2-Methylthio-4-chloro-5, 6-dihydrofuran-[2, 3-d]-pyrimidine

At 125°–130° C., 212.0 g (1.07 mol) of trichloromethyl chloroformate is dripped over a period of 3 hours into a suspension of 65.8 g (0.357 mol) of 2-methylthio-4-hydroxy-5,6-dihydrofuran-[2,3-d]-pyrimidine (Collect. Czech. Chem. Comm., 32, 1582, 1967) in 900 ml of chlorobenzene, three times 0.5 ml of DMF being added. The reaction mixture is stirred for one hour at 130° C. and evaporated down under reduced pressure, and the residue (74 g of an oil) is chromatographed on silica gel (9:1 mixture of toluene and cyclohexane). Yield: 17.0 g of the above product of m.p. 68°–71° C.

2-Methylthio-4-methoxy-5,6-dihydrofuran-[2,3-d]-pyrimidine 17.0 g (84 mmol) of 2-methylthio-4-chloro-5,6-dihydrofuran-[2,3-d]pyrimidine is introduced into 90 ml of methanol. At 45° C., 21.1 g (0.117 mol) of 30% strength sodium methylate solution is dripped in and the whole is stirred for 2 hours at 50° C. The reaction mixture is neutralized to a pH of 6 with a small amount of glacial acetic acid and stirred into 350 ml of ice water. Suction filtration, washing with water and drying give 15.1 g of the above product of m.p. 90°–92° C.

2-Methylsulfonyl-4-methoxy-5,6-dihydrofuran-[2,3-d]-pyrimidine

At 0 to 5° C. and while stirring, chlorine is passed into a mixture of 15.1 g of 2-methylthio-4-methoxy-5,6-dihydrofuran-[2,3-d]-pyrimidine in 120 ml of methylene chloride and 76 ml of water until the reaction mixture is pale yellow. After the mixture has been stirred for 30 minutes the organic phase is separated off and the aqueous phase is extracted with 100 ml of methylene chloride. The combined organic phases are dried and evaporated down. From the residue (16.7 g) there is isolated, after chromatography on silica gel (4:1 mixture of toluene and ethyl acetate) 5.5 g of the above product of m.p. 122°–124° C.

Example 7

Preparation of 2-Methylsulfonyl-4-Methyl-5, 6-Dihydrofuran-[2, 3-d]-Pyrimidine

Analogously to Example 6, the above product (m.p. 85°–90° C.) is obtained in an 80% yield from 2-methylthio-4-methyl-5,6-dihydrofuran-[2,3-d]-pyrimidine (Collect. Czech. Chem. Commun., 32, 1582, 1967).

The sulfones III listed in Table 2 may be similarly obtained.

TABLE 2

| $R^{13}$ | $R^2$ | Phys. data [°C.] |
|---|---|---|
| $CH_3$ | Cl | |
| $CH_3$ | $OCHF_2$ | |
| $CH_3$ | $OC_2H_5$ | |
| $C_6H_5$ | $OCH_3$ | |

Example 8

3-(4-Methoxy-5,6-Dihydrofuran-[2,3-d]-Pyrimidin-2-yl)-Oxy-biphenyl-2-Carboxylic Acid (Compound No. 5.001)

1.57 g (14 mmol) of potassium tert-butylate is added to 1.50 g (7 mmol) of 6-phenylsalicylic acid in 15 ml of anhydrous dimethyl sulfoxide, and the mixture is stirred for 1 hour at room temperature. 1.61 g (7 mmol) of 2-methylsulfonyl-4,6-dimethoxy-5,6-dihydrofuran-[2,3-d]-pyrimidine is added and the reaction mixture is then stirred for 48 hours at room temperature before being poured into 300 ml of water to which 2.5 ml of phosphoric acid has been added. The precipitate is isolated, made into a paste with toluene, and suction filtered. The crude product is stirred for 1 hour in a mixture of 0.5 ml of phosphoric acid and 10 ml of water; after suction filtration and drying there is obtained 1.3 g of the above product of m.p. 176°–178° C.

TABLE 4

Compounds I in which Y is nitrogen

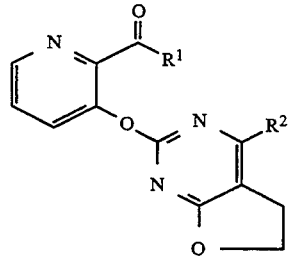

I

| No. | R$^1$ | R$^2$ | Phys. data [°C.] |
|---|---|---|---|
| 4.001 | OH | OCH$_3$ | |
| 4.002 | OCH$_3$ | OCH$_3$ | |
| 4.003 | 2-Propaniminoxy | OCH$_3$ | |
| 4.004 | Propargyloxy | OCH$_3$ | |
| 4.005 | O-(1-pyrazolyl) | OCH$_3$ | |
| 4.006 | O—N(CH$_3$)$_2$ | OCH$_3$ | |

TABLE 3

Compounds I in which Y is carbon

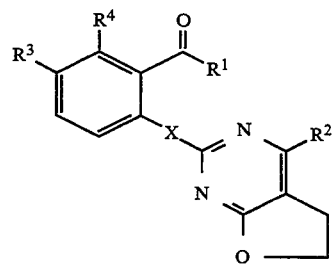

I

| No. | R$^1$ | R$^2$ | X | R$^4$ | R$^3$ | Phys. data mp. [°C.] |
|---|---|---|---|---|---|---|
| 3.001 | OH | CH$_3$ | O | H | H | |
| 3.002 | OCH$_3$ | CH$_3$ | O | H | H | 101–103 |
| 3.003 | OH | CH$_3$ | O | Cl | H | |
| 3.004 | OCH$_3$ | CH$_3$ | O | Cl | H | 124–127 |
| 3.005 | OH | Cl | O | Cl | H | |
| 3.006 | OH | OCH$_3$ | O | H | H | |
| 3.007 | OCH$_3$ | OCH$_3$ | O | H | H | 107 |
| 3.008 | OH | OCH$_3$ | O | Cl | H | 170 |
| 3.009 | OCH$_3$ | OCH$_3$ | O | Cl | H | |
| 3.010 | 2-Propaniminoxy | OCH$_3$ | O | Cl | H | |
| 3.011 | Methylthiomethoxy | OCH$_3$ | O | Cl | H | |
| 3.012 | Propargyloxy | OCH$_3$ | O | Cl | H | |
| 3.013 | OH | OCH$_3$ | S | Cl | H | 155–160 |
| 3.014 | OH | OCH$_3$ | O | F | H | |
| 3.015 | OH | OCH$_3$ | O | OCH$_3$ | H | |
| 3.016 | OH | OCH$_3$ | O | OC$_6$H$_5$ | H | |
| 3.017 | OH | OCH$_3$ | O | SCH$_3$ | H | |
| 3.018 | OH | OCH$_3$ | O | CF$_3$ | H | |
| 3.019 | OH | OCH$_3$ | O | CH=O | H | |
| 3.020 | OH | OCH$_3$ | O | CO$_2$CH$_3$ | H | |
| 3.021 | OH | OCH$_3$ | O | OCHF$_2$ | H | |
| 3.022 | OH | OCH$_3$ | O | CH$_2$=CH—CH=CH$_2$ | | |
| 3.023 | OH | OCH$_3$ | O | N=CH—CH=CH$_2$ | | |
| 3.024 | O-(1-pyrazolyl) | OCH$_3$ | O | Cl | H | |
| 3.025 | O—N(CH$_3$)$_2$ | OCH$_3$ | O | Cl | H | |
| 3.026 | O-(4-morpholinyl) | OCH$_3$ | S | Cl | H | |
| 3.027 | O—P(O)(OC$_2$H$_5$)$_2$ | OCH$_3$ | O | Cl | H | |
| 3.028 | —NH—SO$_2$—CH$_3$ | OCH$_3$ | O | Cl | H | |

TABLE 5

Compounds I in which Y is carbon and R⁴ is a substituted or unsubstituted phenyl radical

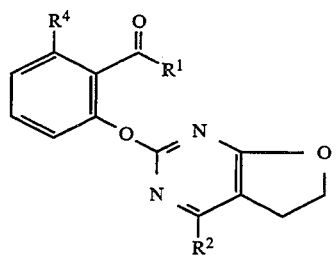

| No. | R¹ | R² | R⁴ | Phys.data mp. [°C.] |
|---|---|---|---|---|
| 5.001 | OH | OCH₃ | Phenyl | 176–178 |
| 5.002 | OCH₃ | OCH₃ | Phenyl | |
| 5.003 | 2-Propaniminoxy | OCH₃ | Phenyl | |
| 5.004 | 1-Imidazolyl | OCH₃ | Phenyl | |
| 5.005 | Methylthiomethoxy | OCH₃ | Phenyl | |
| 5.006 | OH | OCH₃ | 2-Fluorophenyl | |
| 5.007 | OC₂H₅ | OCH₃ | 3-Fluorophenyl | |
| 5.008 | OH | OCH₃ | 4-Fluorophenyl | |
| 5.009 | OH | OCH₃ | 2,6-Difluorophenyl | |
| 5.010 | OH | OCH₃ | 2,4-Difluorophenyl | |
| 5.011 | OH | OCH₃ | 2-Fluoro-4-trifluoromethylphenyl | |
| 5.012 | H | OCH₃ | 2,3-Difluorophenyl | |
| 5.013 | OH | OCH₃ | 2-Chlorophenyl | |
| 5.014 | OC₂H₅ | OCH₃ | 2-Iodophenyl | |
| 5.015 | Methoxyethoxy | OCH₃ | 2-Bromophenyl | |
| 5.016 | OH | OCH₃ | 2-Bromophenyl | |
| 5.017 | OH | OCH₃ | 2-Chloro-6-fluorophenyl | |
| 5.018 | OH | OCH₃ | Pentafluorophenyl | |
| 5.019 | OH | OCH₃ | 2,4-Difluorophenyl | |
| 5.020 | OCH₃ | OCH₃ | 2,4-Dichlorophenyl | |
| 5.021 | OH | OCH₃ | 2,6-Dichlorophenyl | |
| 5.022 | OH | OCH₃ | 2-Chloro-4-fluorophenyl | |
| 5.023 | OH | OCH₃ | 3,5-Dichlorophenyl | |
| 5.024 | 3-Dodecaniminoxy | OCH₃ | 3,5-Dichlorophenyl | |
| 5.025 | OH | OCH₃ | 2-Methylphenyl | |
| 5.026 | OC₂H₅ | OCH₃ | 2-Methylphenyl | |
| 5.027 | Ethylthioethoxy | OCH₃ | 2-Methylphenyl | |
| 5.028 | 1-Imidazolyl | OCH₃ | 2-Methylphenyl | |
| 5.029 | OH | OCH₃ | 2-Chloro-6-methylphenyl | |
| 5.030 | OH | OCH₃ | 3-Methylphenyl | |
| 5.031 | OH | OCH₃ | 4-Methylphenyl | |
| 5.032 | OH | OCH₃ | 2,6-Dimethylphenyl | |
| 5.033 | OH | OCH₃ | 3,5-Dimethylphenyl | |
| 5.034 | OH | OCH₃ | 2,4,6-Trimethylphenyl | |
| 5.035 | OC₂H₅ | OCH₃ | 2,4,6-Trimethylphenyl | |
| 5.036 | OH | OCH₃ | 2,4-Dimethylphenyl | |
| 5.037 | OH | OCH₃ | 2-Chloro-4-methylphenyl | |
| 5.038 | OH | OCH₃ | 2,3,5-Trichlorophenyl | |
| 5.039 | OH | OCH₃ | 4-Methoxyphenyl | |
| 5.040 | OH | OCH₃ | 2-Methoxyphenyl | |
| 5.041 | OH | OCH₃ | 4-Chloro-2-methoxyphenyl | |
| 5.042 | OH | OCH₃ | 2-Trifluoromethylphenyl | |
| 5.043 | OH | OCH₃ | 2,3-Dimethyl-4-methoxyphenyl | |
| 5.044 | OH | OCH₃ | 2-Dimethylamino-2-methylphenyl | |
| 5.045 | OH | OCH₃ | 3-Cyanophenyl | |
| 5.046 | OC₂H₅ | OCH₃ | 3-Nitrophenyl | |
| 5.047 | OH | OCH₃ | 3-Phenoxyphenyl | |
| 5.048 | OH | OCH₃ | 3-(3-Trifluoromethylphenoxy)-phenyl | |
| 5.049 | OH | OCH₃ | 3-Trifluoromethylphenyl | |
| 5.050 | OCH₃ | OCH₃ | 3-Trifluoromethylphenyl | |
| 5.051 | OH | OCH₃ | 3-Bromophenyl | |
| 5.052 | OH | OCH₃ | 3-Chlorophenyl | |
| 5.053 | OH | OCH₃ | 4-Bromophenyl | |
| 5.054 | OH | OCH₃ | 4-Chlorophenyl | |
| 5.055 | OH | OCH₃ | 4-Trifluoromethylphenyl | |
| 5.056 | OH | OCH₃ | 3-(3,4-Dichlorophenoxy)phenyl | |
| 5.057 | OH | OCH₃ | 4-Methylthiophenyl | |
| 5.058 | O-(1-pyrazolyl) | OCH₃ | Phenyl | |
| 5.059 | O-(1-imidazolyl) | OCH₃ | Phenyl | |
| 5.060 | O—N(CH₃)₂ | OCH₃ | Phenyl | |
| 5.061 | O—NH—C(CH₃)₃ | OCH₃ | Phenyl | |
| 5.062 | O-(1-piperidinyl) | OCH₃ | Phenyl | |
| 5.063 | O-(4-morpholinyl) | OCH₃ | Phenyl | |
| 5.064 | O—P(O)(OCH₃)₂ | OCH₃ | Phenyl | |

TABLE 5-continued

Compounds I in which Y is carbon and $R^4$ is a substituted or unsubstituted phenyl radical

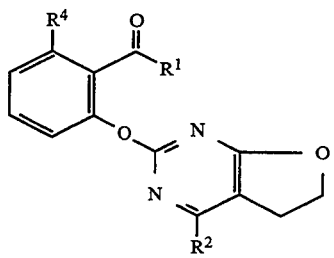

I

| No. | $R^1$ | $R^2$ | $R^4$ | Phys.data mp. [°C.] |
|---|---|---|---|---|
| 5.065 | NH—SO₂—C₆H₄-4-CH₃ | OCH₃ | Phenyl | |

TABLE 6

Compounds I in which $R^4$ is a heterocyclic radical and Y is carbon

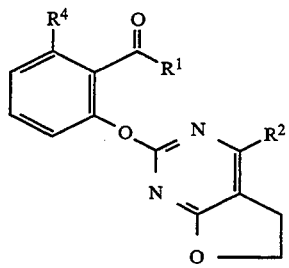

I

| No. | $R^1$ | $R^2$ | $R^4$ | Phys. data mp. [°C.] |
|---|---|---|---|---|
| 6.001 | OH | OCH₃ | Pyrazol-1-yl | 169–172, decomp. |
| 6.002 | OC₂H₅ | OCH₃ | Pyrazol-1-yl | |
| 6.003 | OC₂H₅ | OCH₃ | 4-Methylpyrazol-1-yl | |
| 6.004 | OC₂H₅ | OCH₃ | 3,5-Dimethylpyrazol-1-yl | |
| 6.005 | OH | OCH₃ | 3,5-Dimethylpyrazol-1-yl | |
| 6.006 | OH | OCH₃ | 3(5)-Methylpyrazol-1-yl | |
| 6.007 | OH | OCH₃ | 4-Methylpyrazol-1-yl | |
| 6.008 | OC₂H₅ | OCH₃ | 4-Chloropyrazol-1-yl | |
| 6.009 | OH | OCH₃ | 4-Chloropyrazol-1-yl | |
| 6.010 | OH | OCH₃ | 4-Bromopyrazol-1-yl | |
| 6.011 | OH | OCH₃ | 4-Phenylpyrazol-1-yl | |
| 6.012 | OC₂H₅ | OCH₃ | 4-Phenylpyrazol-1-yl | |
| 6.013 | OH | OCH₃ | 3,4,5-Trimethylpyrazol-1-yl | |
| 6.014 | OH | OCH₃ | 4-Chloro-3,5-dimethylpyrazol-1-yl | |
| 6.015 | OH | OCH₃ | 4-Isopropylpyrazol-1-yl | |
| 6.016 | OH | OCH₃ | 3(5)-Phenylpyrazol-1-yl | |
| 6.017 | OH | OCH₃ | 3(5)-Methyl-5(3)-phenylpyrazol-1-yl | |
| 6.018 | OH | OCH₃ | 3,5-Bistrifluoromethylpyrazol-1-yl | |
| 6.019 | OH | OCH₃ | 4-Nitropyrazol-1-yl | |
| 6.020 | Methylthiomethoxy | OCH₃ | Pyrazol-1-yl | |
| 6.021 | Methoxyethoxy | OCH₃ | Pyrazol-1-yl | |
| 6.022 | OCH₂—CO—OC₂H₅ | OCH₃ | Pyrazol-1-yl | |
| 6.023 | OH | OCH₃ | Imidazolyl-1-yl | |
| 6.024 | OH | OCH₃ | 2-Methylimidazol-1-yl | |
| 6.025 | OH | OCH₃ | 4,5-Dimethylimidazol-1-yl | |
| 6.026 | OH | OCH₃ | 2-Phenylimidazol-1-yl | |
| 6.027 | OH | OCH₃ | 4,5-Dichloroimidazol-1-yl | |
| 6.028 | OH | OCH₃ | 2,4,5-Trichloroimidazol-1-yl | |
| 6.029 | OH | OCH₃ | 2-Methyl-4,5-dichloroimidazol-1-yl | |
| 6.030 | OH | OCH₃ | 2-Methyl-4,5-dibromoimidazol-1-yl | |
| 6.031 | OH | OCH₃ | 4(5)-Chloro-5(4)-methylimidazol-1-yl | |
| 6.032 | OH | OCH₃ | 4(5)-Nitroimidazol-yl | |
| 6.033 | OH | OCH₃ | (1,2,4)-Triazol-1-yl | |
| 6.034 | OH | OCH₃ | 3(5)-Methyl-[1,2,4]-triazol-1-yl | |
| 6.035 | OH | OCH₃ | 3(5)-Phenyl-[1,2,4]-triazol-1-yl | |
| 6.036 | OH | OCH₃ | 3,5-Dimethyl-[1,2,4]-triazol-1-yl | |
| 6.037 | OH | OCH₃ | [1,2,3]-Triazol-1-yl | |
| 6.038 | OH | OCH₃ | 4,5-Dimethyl-[1,2,3]-triazol-1-yl | |
| 6.039 | OH | OCH₃ | 4(5)-Phenyl-[1,2,3]-triazol-1-yl | |
| 6.040 | OH | OCH₃ | [1,2,3,4]-Tetrazol-1-yl | |
| 6.041 | OC₂H₅ | OCH₃ | 1-Methylpyrazol-4-yl | |
| 6.042 | OC₂H₅ | OCH₃ | 1-Phenylpyrazol-4-yl | |

TABLE 6-continued

Compounds I in which R⁴ is a heterocyclic radical and Y is carbon

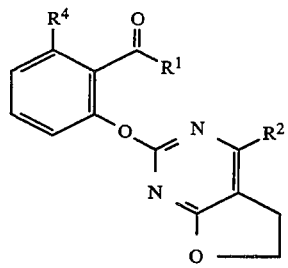

| No. | R¹ | R² | R⁴ | Phys. data mp. [°C.] |
|---|---|---|---|---|
| 6.043 | OH | OCH₃ | 1-Phenylpyrazol-4-yl | |
| 6.044 | OC₂H₅ | OCH₃ | 1,3,5-Trimethylpyrazol-4-yl | |
| 6.045 | OH | OCH₃ | 1,3,5-Trimethylpyrazol-4-yl | |
| 6.046 | OH | OCH₃ | 1-Methylpyrazol-4-yl | |
| 6.047 | OH | OCH₃ | 1-Methylpyrazol-5-yl | |
| 6.048 | OH | OCH₃ | 1-Phenylpyrazol-5-yl | |
| 6.049 | OH | OCH₃ | 1-Methylpyrazol-3-yl | |
| 6.050 | OH | OCH₃ | 1-Phenylpyrazol-3-yl | |
| 6.051 | OC₂H₅ | OCH₃ | 1-Methylpyrazol-3-yl | |
| 6.052 | OH | OCH₃ | 1,4-Dimethylpyrazol-3-yl | |
| 6.053 | OH | OCH₃ | 5-Methyl-1-phenylpyrazol-3-yl | |
| 6.054 | OH | OCH₃ | 1,5-Dimethylpyrazol-3-yl | |
| 6.055 | OH | OCH₃ | 1,3-Dimethylpyrazol-4-yl | |
| 6.056 | OH | OCH₃ | 1,5-Dimethylpyrazol-4-yl | |
| 6.057 | OH | OCH₃ | 3-Methyl-1-phenylpyrazol-4-yl | |
| 6.058 | OH | OCH₃ | 5-Methyl-1-phenylpyrazol-4-yl | |
| 6.059 | OH | OCH₃ | 3,5-Dimethyl-1-phenylpyrazol-4-yl | |
| 6.060 | OH | OCH₃ | 3-Methyl-1-phenylpyrazol-5-yl | |
| 6.061 | OH | OCH₃ | 1,4-Dimethylpyrazol-5-yl | |
| 6.062 | OH | OCH₃ | 1,3-Dimethylpyrazol-5-yl | |
| 6.063 | OH | OCH₃ | 1-Methyl-[1,2,3]-triazol-5-yl | |
| 6.064 | OH | OCH₃ | 1-Phenyl-[1,2,3]-triazol-5-yl | |
| 6.065 | OH | OCH₃ | 1-Phenyl-[1,2,3]-triazol-4-yl | |
| 6.066 | OH | OCH₃ | 5-Methyl-1-phenyl-[1,2,3]-triazol-4-yl | |
| 6.067 | OH | OCH₃ | 5-Methyl-1-phenyl-[1,2,4]-triazol-3-yl | |
| 6.068 | OC₂H₅ | OCH₃ | 1-Methylimidazol-2-yl | |
| 6.069 | OH | OCH₃ | 1-Methylimidazol-2-yl | |
| 6.070 | OH | OCH₃ | 1,4-Dimethylimidazol-5-yl | |
| 6.071 | OH | OCH₃ | 1-Methyl-5-nitroimidazol-2-yl | |
| 6.072 | OH | OCH₃ | 1-Methylimidazol-5-yl | |
| 6.073 | OH | OCH₃ | 1-Phenylimidazol-5-yl | |
| 6.074 | OH | OCH₃ | 2-Thienyl | |
| 6.075 | OH | OCH₃ | 3-Thienyl | |
| 6.076 | OH | OCH₃ | 2,3-Dichloro-4-thienyl | |
| 6.077 | OH | OCH₃ | 2,5-Dichloro-3-thienyl | |
| 6.078 | OH | OCH₃ | 2-Bromo-5-thienyl | |
| 6.079 | OH | OCH₃ | 4-Bromo-2-thienyl | |
| 6.080 | OH | OCH₃ | 3-Methyl-2-thienyl | |
| 6.081 | OH | OCH₃ | 2-Chloro-5-thienyl | |
| 6.082 | OH | OCH₃ | 2-Methyl-5-thienyl | |
| 6.083 | O-(1-pyrazolyl) | OCH₃ | Pyrazol-1-yl | |
| 6.084 | O-(1-imidazolyl) | OCH₃ | Pyrazol-1-yl | |
| 6.085 | O—N(CH₃)₂ | OCH₃ | Pyrazol-1-yl | |
| 6.086 | O—NH—C(CH₃)₃ | OCH₃ | Pyrazol-1-yl | |
| 6.087 | O-(1-piperidinyl) | OCH₃ | Pyrazol-1-yl | |
| 6.088 | (4-morpholinyl) | OCH₃ | Pyrazol-1-yl | |
| 6.089 | O-(1-pyrazolyl) | OCH₃ | Imidazol-1-yl | |
| 6.090 | O—N(CH₃)₂ | OCH₃ | Imidazol-1-yl | |
| 6.091 | O-(4-morpholinyl) | OCH₃ | Imidazol-1-yl | |
| 6.092 | O-(1-pyrazolyl) | OCH₃ | 2-Thienyl | |
| 6.093 | O-(1-imidazolyl) | OCH₃ | 3-Thienyl | |
| 6.094 | O—N(CH₃)₂ | OCH₃ | 2-Thienyl | |
| 6.095 | O—NH—C(CH₃)₃ | OCH₃ | 2-Thienyl | |
| 6.096 | O-(1-piperidinyl) | OCH₃ | 3-Thienyl | |
| 6.097 | O-(4-morpholinyl) | OCH₃ | 2-Thienyl | |
| 6.098 | O—P(O)(OC₂H₅)₂ | OCH₃ | 2-Thienyl | |
| 6.099 | NH—SO₂—C₆H₄—CH₃ | OCH₃ | 1-Pyrazolyl | |

TABLE 7

Compounds I in which R⁴ is a naphthyl or quinolinyl radical and Y is carbon

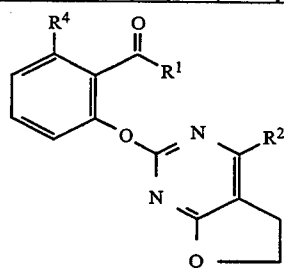

| No. | $R^1$ | $R^2$ | $R^4$ | Phys. data mp. [°C.] |
|---|---|---|---|---|
| 7.001 | OH | OCH₃ | 1-Naphthyl | |
| 7.002 | OH | OCH₃ | 2-Naphthyl | |
| 7.003 | OH | OCH₃ | 2-Chloro-1-naphthyl | |
| 7.004 | OH | OCH₃ | 6-Chloro-1-naphthyl | |
| 7.005 | OH | OCH₃ | 2,6-Dichloro-1-naphthyl | |
| 7.006 | OH | OCH₃ | 2-Methyl-1-naphthyl | |
| 7.007 | OH | OCH₃ | 6-Chloro-2-methyl-1-naphthyl | |
| 7.008 | OH | OCH₃ | 2-Quinolinyl | |
| 7.009 | OH | OCH₃ | 6-Quinolinyl | |
| 7.010 | OH | OCH₃ | 2-Methyl-6-quinolinyl | |
| 7.011 | OCH₃ | OCH₃ | 1-Naphthyl | |
| 7.012 | OCH₃ | OCH₃ | 2-Naphthyl | |
| 7.013 | 2-Propaniminoxy | OCH₃ | 1-Naphthyl | |
| 7.014 | Propargyloxy | OCH₃ | 2-Naphthyl | |
| 7.015 | 1-Imidazolyl | OCH₃ | 1-Naphthyl | |
| 7.016 | O-(1-pyrazolyl) | OCH₃ | 1-Naphthyl | |
| 7.017 | O—N(CH₃)₂ | OCH₃ | 2-Naphthyl | |
| 7.018 | O-(4-morpholinyl) | OCH₃ | 1-Naphthyl | |
| 7.019 | O—P(O)(OC₂H₅)₂ | OCH₃ | 1-Naphthyl | |
| 7.020 | NH—SO₂—C₆H₄-4-CH₃ | OCH₃ | 2-Naphthyl | |

Examples Illustrating Herbicidal Action

The herbicidal action of the carboxylic acid derivatives of the formula I is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the active ingredients, suspended or emulsified in water.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were *Abutilon theophrasti*, *Amaranthus retroflexus* and *Solanum nigrum*.

Compounds 3.008 and 3.013, applied postemergence at a rate of 0.06 kg/ha, provided excellent control of unwanted plants.

We claim:

1. A novel sulfone of the formula III

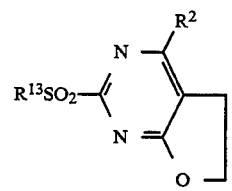

where $R^2$ is $C_1$–$C_4$-alkyl, $C_1$–$C_4$-alkoxy, $C_1$–$C_4$-haloalkoxy or halogen and $R^{13}$ is $C_1$–$C_{12}$-alkyl or is phenyl which is unsubstituted or substituted by alkyl, halogen or alkoxy.

2. A sulfone as defined in claim 1, wherein $R^2$ is methoxy.

* * * * *